(12) United States Patent
Adams et al.

(10) Patent No.: US 6,927,849 B2
(45) Date of Patent: Aug. 9, 2005

(54) OPTICAL FIBER COATING DEFECT DETECTOR

(75) Inventors: Ronald L. Adams, Buford, GA (US); Harry D. Garner, Lawrenceville, GA (US); Robert Thornton, Cumming, GA (US)

(73) Assignee: Furukawa Electric North America, Inc., Atlanta, GA (US)

( * ) Notice: Subject to any disclaimer, the term of this patent is extended or adjusted under 35 U.S.C. 154(b) by 373 days.

(21) Appl. No.: 10/278,372

(22) Filed: Oct. 23, 2002

(65) Prior Publication Data

US 2004/0080743 A1 Apr. 29, 2004

(51) Int. Cl.[7] .............................................. G01N 21/88
(52) U.S. Cl. ................................. 356/239.2; 356/73.1
(58) Field of Search ........................... 356/73.1, 237.1, 356/237.2–237.5, 429–431, 239.1, 239.2

(56) References Cited

U.S. PATENT DOCUMENTS 5,436,719 A   7/1995  Doles et al. ............... 356/73.1
5,469,252 A   11/1995 Doles et al. ............... 356/73.1

FOREIGN PATENT DOCUMENTS

CA   2084819       7/1993
EP   0553987 A1   8/1993   .......... G01N/21/41

Primary Examiner—Richard A. Rosenberger
Assistant Examiner—Vincent P. Barth
(74) Attorney, Agent, or Firm—Thomas, Kayden, Horstemeyer & Risley, LLP

(57) ABSTRACT

A monitoring system for detection of defects in an optical fiber coating during production of the fiber has first and second beam generating means which produce planar coherent beams which cross each other at the fiber passing through the system creating one or more diffraction patterns. A first plurality of photodetectors are mounted in a mount, the front face of which is impinged by the planar diffraction pattern, and a second plurality of photodetectors is similarly mounted in position below the impinging pattern. A defect in the fiber coating, regardless of shape or orientation, will cause the pattern or patterns to be tilted or shifted upward, downward, or planarly tilted to impinge one or more of the photodiodes which, as a result, generates a signal which is applied to a comparator and control circuit.

8 Claims, 3 Drawing Sheets

Fig. 3b   Fig. 3c

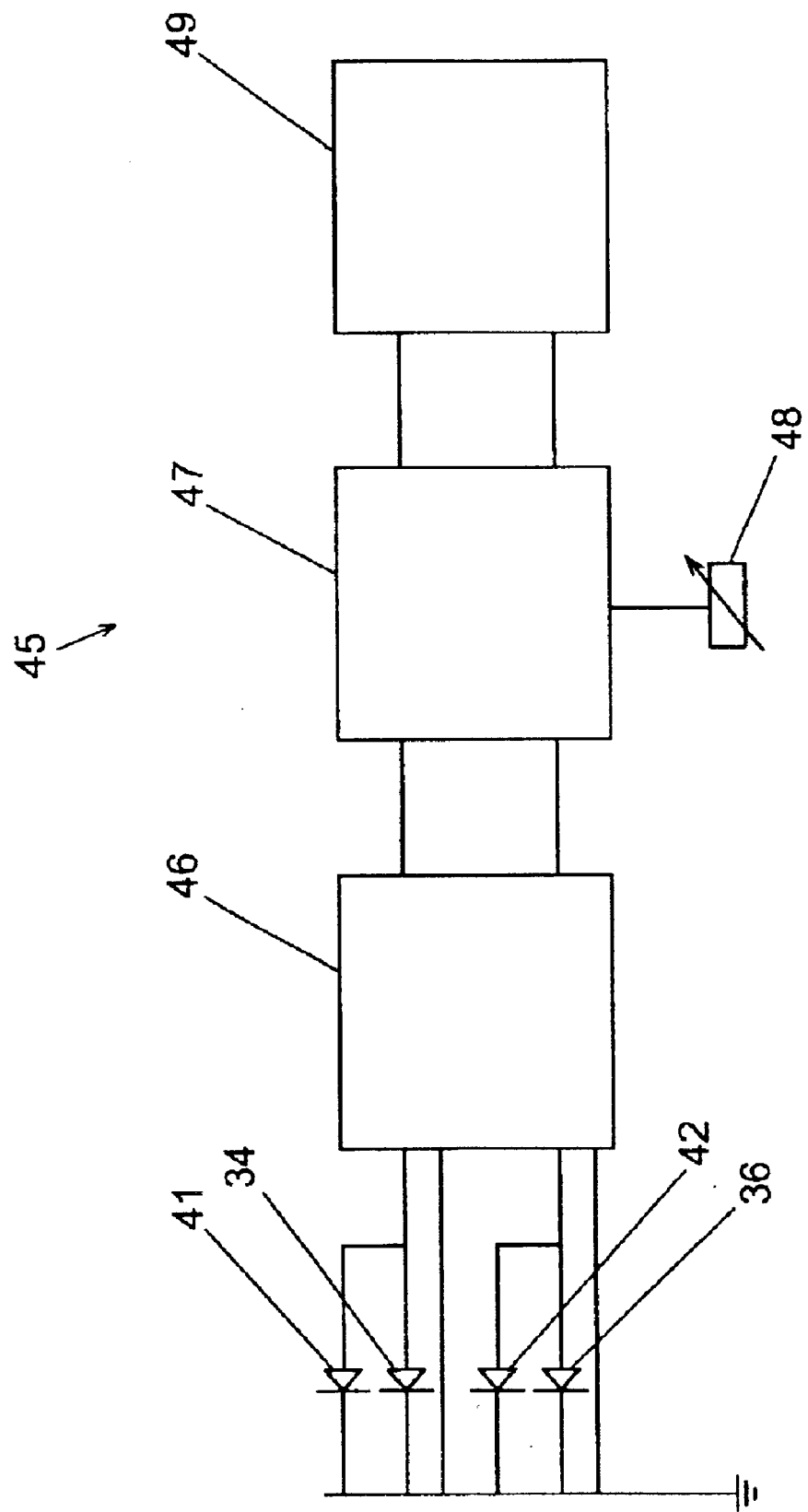

OPTICAL FIBER COATING DEFECT DETECTOR

RELATED APPLICATIONS

The invention disclosed herein is related to European Patent EP0553987 of Frazee, et al.

FIELD OF THE INVENTION

This invention relates to an on-line optical fiber coating defect detection system.

BACKGROUND OF THE INVENTION

The increasing use of optical fiber in optical communications systems has resulted in a demand for extremely large quantities of fiber. In the production of suitable fibers, a continuous process for drawing the fiber from a heated to softness glass preform at relatively high speeds, such as, for example, thirty-five meters per second, (35 m/sec.) is almost universally used. It is also the common practice that, during the draw process, a coating of, preferably, polymeric material, is applied to the fiber. This coating functions to protect the glass fiber from nicks, scratches, and other environmental concerns, and further, increases the structural strength of the fiber when so coated.

There are strict operational constraints that apply to glass fibers in use in, for example, an optical communication system, thus, the fiber manufacturing process is, customarily, closely monitored and controlled to eliminate defects in the fiber occurring during the draw process. The coating on the fiber, if faulty, can also have a deleterious effect on the fiber performance, hence the coating application process should be closely monitored also. Thus, monitoring of the coating is directed primarily to such parameters as diameter, elliptically, and concentricity, which are slow changing parameters and can be detected and evaluated over considerable fiber lengths. In general, devices employing various scanning techniques are utilized to monitor these slow changing parameters. However, the particular devices presently used to identify and measure these slow changing parameters are not capable of accurately identifying and responding to defects which are temporarily short in duration at line draw speeds and thus quite often such defects escape detection by present day monitors which employ scanning techniques. Such defects may be caused by inclusion of particulates, which may alter the coating diameter, entrapped bubbles, or high viscosity areas in the coating pulled through the coating application die or by the particular shape or configuration of the defect. Each of these defects, as well as others, may cause a loss of lightguide product during subsequent processing. The only such defects that existing devices consistently and accurately detect are those which happen to be exceptionally large.

In European patent EPO 553987 Al of Frazee, et al., of previously common assignee, the disclosure of which is incorporated by reference herein, there is shown and described a monitoring apparatus which applies one or more orthogonally intersecting light beams to a coated fiber. As the light passes through the fiber and coating, a refraction pattern having a predictable intensity level is produced by the forward scattered light beams. The intensity of the forward scattered pattern is continuously monitored by a plurality of photo-diodes. Various defects in the coating cause the light path through the coating to be altered, thereby directing some of the forward scattered light outside of the normal pattern into the detection area of the photo-diodes, producing an increase in the light intensity measured by these diodes, thus indicating the presence of forward scatter produced by short defects in the coating.

SUMMARY OF THE INVENTION

The present invention is a monitoring system that is substantially completely insensitive to the orientation or shape of the defect, thereby eliminating that parameter as a factor.

In a preferred embodiment of the invention, the diffraction pattern is a substantially planar spreading sheet which, in this embodiment, is horizontal with respect to a support base for the monitoring apparatus. First, second, third and fourth detector diodes are aligned and oriented above the plane of the pattern, and fifth, six, seventh, and eighth detector diodes are aligned below the plane of the pattern. The diodes are located outside of the laser beam axes as opposed to some prior art devices which make diode measurements along the beam axis. In use, the forward scatter due to a defect will cause the plane of the pattern, or a portion thereof, to tilt upward whereby the first through fourth diodes detect the resulting increased illumination to register a defect. The diodes below the plane are unaffected. If, however, the shape or orientation of the defect causes the plane or portion thereof to tilt down (back scatter) the fifth through eighth diodes will detect the increased illumination while the first through fourth diodes are unaffected, thereby registering a defect which, were only front scattering relied upon, as in the prior art, would be undetected. The unique arrangement of detectors is also capable of detecting defects which, because of their orientation and shape, might cause the plane of the pattern, or a portion thereof, to tilt sideways instead of entirely up or down. In addition, the arrangement of detectors operates effectively regardless of the direction of movement of the fiber through the monitoring apparatus.

In greater detail, the preferred embodiment comprises first and second lasers mounted on a base and emitting parallel beams in the same direction. A system of mirrors directs the beams to a region where they orthogonally intersect, and the fiber being monitored passes through the intersection. Beyond the intersection are mounted the aligned first and second and the aligned fifth and sixth diodes in a plane orthogonal to one of the beams and the aligned third and fourth and aligned seventh and eighth diodes are mounted in a plane orthogonal to the other beam. The first and second diodes are situated above the fifth and sixth diodes, and the third and fourth diode are situated above the seventh and eighth diodes.

The preferred embodiment may also be modified to use a single laser and a beam splitter to create two beams as shown in the aforementioned Frazee, et al. European patent.

The outputs of the several diodes are applied to suitable electronic circuitry for generating a signal or signals indicating a defect and for producing other signals, where necessary or desired, to, for example, stop the moving fiber, or indicate where the defect in the fiber is located.

The monitoring system of the invention thus utilizes an out of pattern technique for measuring an increase in light intensity impinging on photodetectors positioned above and below the expected scatter pattern when a defect is present, regardless of shape or orientation of the defect and of the direction of passage of the fiber through the monitor.

These and other features of the present invention will be more readily apparent from the following detailed description, read in conjunction with the accompanying drawings.

DESCRIPTION OF THE DRAWINGS

FIGS. 3b and 3c are diagrams of the defect detection operation utilizing the diffraction patterns of FIG. 3a; and FIG. 4 is a block diagram of the electrical system which responds to the detection of the defects in the fiber coating.

DETAILED DESCRIPTION

Figure 1:
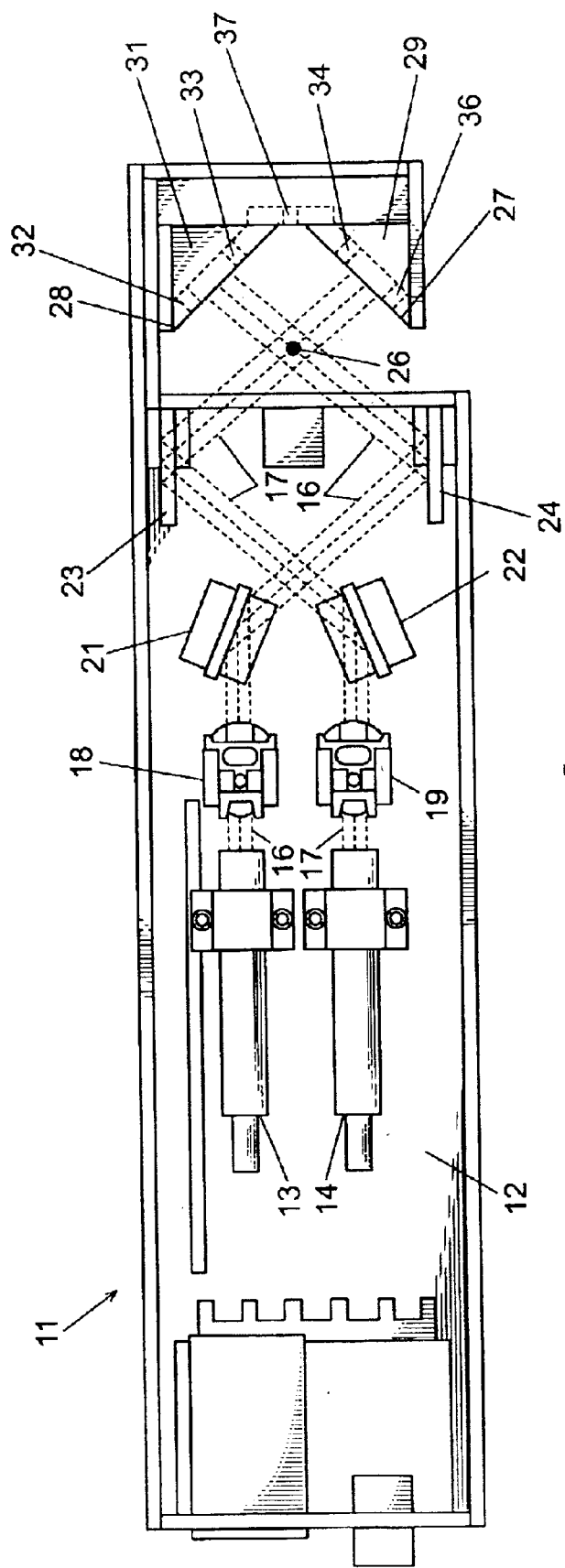
FIG. 1 is a plan view of the electro-optic monitoring system of the present invention.

FIG. 1 depicts an opto-electronic embodiment 11 of the present invention, comprising a base member 12 having mounted thereon first and second lasers 13 and 14 parallel to each other. Lasers 13 and 14 may be any of a number of laser types, such as, for example, diode lasers. Lasers 13 and 14 generate parallel light beams 16 and 17 respectively which are directed into and through beam expanders 18 and 19 which collimate and expand the width of the beam 16 and 17 to, for example, a six millimeter (mm) width thereby forming a substantially planar sheet collimated beam. The expanded beams are directed to first and second mirrors 21 and 22 which, in turn, direct the beam to third and fourth mirrors 23 and 24 which direct the beams to an orthogonal crossing at the fiber 26 which passes through the cross-point in a direction perpendicular to the plane of the base 12. The mirrors 21 and 22 are shown as being adjustable so as to align the beams to cross at the desired point, i.e., the fiber 26 location. It is also possible, if desired, to make mirrors 23 and 24 adjustable also, although mirrors 21 and 22 have a range of adjustments adequate to achieve the desired precision in locating the orthogonal crossing of the beams 16 and 17 at the fiber 26. The light beams 16 and 17, passing through the coated fibers 26 generate a scatter or diffraction pattern which impinges on the planar faces 27 and 28 of first and second detector mountings 29 and 31 each of which, as will be more apparent hereinafter, contains four defect detection diodes. In FIG. 1, only two diodes 32 and 33 are shown in mount 29, and two 34 and 36 in mount 31, the remaining two diodes in each mount 29 and 31 being located directly beneath those shown, as will be discussed hereinafter. An axially aligned photo-detector 37 functions to detect the presence of a laser illuminated coated fiber 26 by monitoring a pattern from each beam axis generated when light passes through the fiber and coating.

Figure 2:
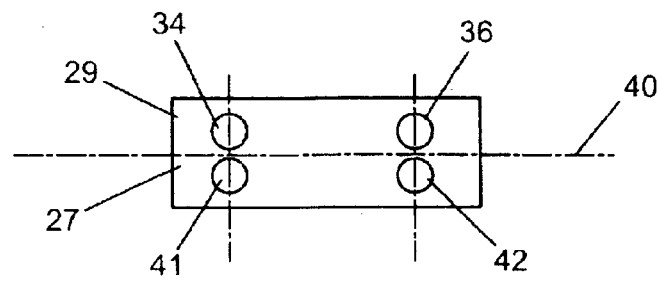
FIG. 2 is a front elevation view of a component of the system of FIG. 1.

FIG. 2 is an elevation view of the planar face 27 of detector mounting 29. It is to be understood that face 28 of mounting 31 is substantially identical to that shown in FIG. 2. Mounting 29 has, as pointed out whereinbefore, first and second spaced diode defect detectors 34 and 36, mounted slightly above the centerline 40 of face 27, and third and fourth spaced defect detectors 41 and 42 mounted slightly below centerline 40. Detectors 34, 36, 41, and 42 are preferably photo-detectors having good high frequency response and sensitivity, and preferably low cost. The active detection area of each detector diode is, preferably, approximately one millimeter (1 mm) square, and they generate a signal in response to the diffracted beams 16 and 17 impinging thereon.

Figure 3A:
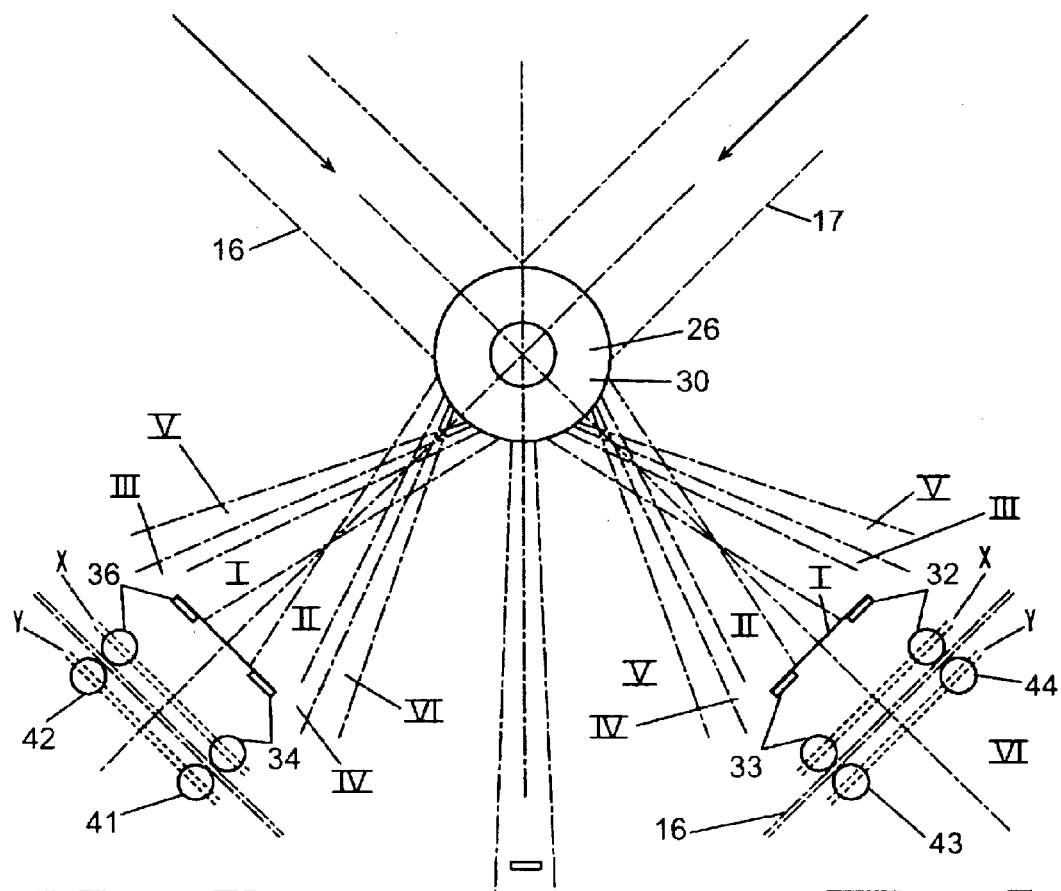
FIG. 3a is a diagram of a portion of the diffraction pattern as formed by the system and apparatus of FIG. 1.

FIG. 3a is a diagram of the diffraction pattern resulting from beams 16 and 17 impinging on and passing through the coating 30 of fiber 26. The diagram of FIG. 3a is not intended to depict the entire diffraction pattern, but only the portions thereof affecting the operation of the system. As can be seen in FIG. 3a, there are two substantially identical diffraction patterns emerging from coated fiber 26. Each pattern has regions I and II of light, bordered on one side by dark regions III and IV which are in turn bordered by light regions V and VI. The diode detectors 32–34 and 36 and 41–44 are positioned to detect the portion of the light in regions I and II, i.e., off axis illumination, or seen in FIGS. 3b and 3c, and are situated above and below the beams 16 and 17, also as shown in FIGS. 3b and 3c. As was pointed out hereinbefore, a defect causing forward scatter will cause the plane of the pattern to tilt upward to, for example, position X, and as shown in dashed lines, in both FIGS. 3b and 3c where it is detected by diodes 32, 33, 34, or 36. The configuration or location of the defect may cause only one of the patterns, e.g., that of beam 17, to be tilted, while that of beam 16 is unaffected, or vise versa. Nonetheless, the diodes will detect the defect. In a similar manner, if the configuration or location of the defect may cause the plane of the pattern, to tilt down to or toward position Y because of back scatter, as shown in the dot-dash lines in FIGS. 3b and 3c, and the diodes 41, 42, 43, and/or 44 will detect the defect. As with forward scatter, only one of the patterns may be tilted, yet the defect will still be detected. Also, it can be appreciated that one or both patterns may be tilted in the plane of the drawing, i. e., about an axis perpendicular to the plane of the paper, and a defect will still be registered. It can be appreciated, therefore, that with the configuration and location of the photo-detectors, virtually any defect, regardless of location, shape, or size, will be detected.

In the foregoing, the terms "up" and "down" are applied to the figures as drawn and are not meant to be restrictive as to the system orientation.

Photodiode 37 is used to detect the presence of a laser illuminated coated fiber by monitoring a pattern from each axis generated when the light impinging upon the fiber is scattered by the cylindrical coating layer 30.

FIG. 4 is a block diagram of the utilization of the signals of the photo-diodes 34, 36, 41, and 42 for controlling the draw process in the event of detection of a coating defect by the detector in the detector arrangement in mounting 29. A similar arrangement is connected to the detector of mounting 28 or they may be ganged together. The arrangement of FIG. 4 comprises an amplifier 46 which receives the input signals from the photodiodes 34, 36, 41, and after amplification, applies them to a comparator 47, which also receives a reference voltage from an adjustable source 48. The reference voltage is adjusted to establish the desired sensitivity of the system. The comparator 47 compares to signal input to the reference voltage and generates, in the event of a detected defect, a defect signal which is applied to a processing unit 49 which may be programmed to stop the coating process, to mark the defect location, or other desired control of the process.

From the foregoing, it can be seen that the monitoring system of the present invention detects defects in a fiber coating regardless of orientation or shape thereof, regardless of the direction of movement of the fiber. Further, the apparatus itself is compact and can thus be place din any desired location along the path of the moving fiber.

It is to be understood that the various features of the present invention might readily be incorporated into other types of monitoring arrangements, and that other modifications or adaptations might occur to workers in the art. All such variations and modifications are intended to be included herein as being within the scope of the invention as set forth. Further, in the claims hereinafter, the corresponding structures, materials, acts, and equivalents of all means or step-plus-function elements are intended to include any structure, materials, acts, or acts for performing the functions in combination with other elements as specifically claimed.

What is claimed is:

1. A monitoring apparatus for detecting defects in the coating layer of an optical fiber comprising:

an optical apparatus for producing first and second collimated planar sheet light beams which intersect at a point through which the fiber passes, thereby illuminating the coating thereof and creating at least one planar sheet diffraction pattern;

a mounting member adapted to be impinged by said planar sheet diffraction pattern in a planar sheet impingement pattern;

said mounting member having a first pair of spaced optical detection devices positioned on one planar side of the line of impingement pattern; and a second pair of spaced optical detection devices positioned on the other planar side of the line of impingement pattern said first pair.

2. A monitoring apparatus as claimed in claim 1 and further including an electrical processing circuit for receiving signals indicative of a defect in the coating layer from any of said optical detection devices upon which the planar sheet pattern impinges, and producing an output indicating the presence of a defect.

3. A monitoring apparatus as claimed in claim 2 and further including a control circuit for receiving the output of said processing circuit for controlling the fiber coating process.

4. A monitoring apparatus as claimed in claim 1 wherein said optical apparatus comprises first and second lasers for emitting beams, and a beam expander in the path of each beam for creating an expanded substantially planar sheet collimated planar beam.

5. A monitoring apparatus as claimed in claim 4 wherein said optical apparatus further comprises first and second angled reflecting members in the paths of said planar beams for directing them to third and fourth reflecting members which direct them to an orthogonal crossing at a point through which the coated optical fiber passes.

6. A monitoring apparatus as claimed in claim 1 and further including an axially aligned photodetector for indicating the presence of the optical fiber passing through the monitoring apparatus.

7. A monitoring apparatus as claimed in claim 1 wherein each of said optical detection devices of said second pair is aligned with a corresponding optical detection device of said first pair.

8. A monitoring apparatus as claimed in claim 1 wherein said optical apparatus comprises at least one laser.

* * * * *